United States Patent [19]

Fock et al.

[11] Patent Number: 5,026,902

[45] Date of Patent: Jun. 25, 1991

[54] DENTAL COMPSITION OF PERFLUOROALKYL GROUP-CONTAINING (METH-)ACRYLATE ESTERS

[75] Inventors: Jürgen Fock, Düsseldorf; Günter Hahn, Mühlheim/Ruhr; Günter Wagenknecht, Echzell, all of Fed. Rep. of Germany

[73] Assignee: Th. Goldschmidt AG & GDF Gesellschaft für Dentale Forschung ü. Innovationen GmbH, Essen, Fed. Rep. of Germany

[21] Appl. No.: 441,764

[22] Filed: Nov. 27, 1989

[30] Foreign Application Priority Data

Dec. 10, 1988 [DE] Fed. Rep. of Germany ....... 3844619

[51] Int. Cl.$^5$ .............................................. C07C 69/54
[52] U.S. Cl. ...................................... 560/223; 106/35
[58] Field of Search ........................... 560/223; 106/35

[56] References Cited

U.S. PATENT DOCUMENTS 3,660,360  5/1972  Ray-Chaudhuri et al. ......... 560/223
4,080,507  3/1978  Gresham ............................ 560/223

Primary Examiner—Paul J. Killos
Attorney, Agent, or Firm—Toren, McGeady & Associates

[57] ABSTRACT

A dental preparation is disclosed which comprises a (meth-)acrylate ester of the general formula

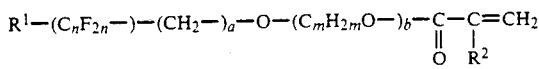

wherein
R$^1$ is the same or different and represents a hydrogen or fluorine group
R$^2$ is the same or different and represents a hydrogen or methyl group,
a has a value of 0, 1, 2, 3 or 4,
b has an average value of 2 to 30,
n has an average value of 4 to 12 and
m has an average value of 3 to 14.

The preparation is, for example, suitable as relining material for dental prostheses.

1 Claim, No Drawings

DENTAL COMPOSITION OF PERFLUOROALKYL GROUP-CONTAINING (METH-)ACRYLATE ESTERS

Field of Invention

The invention is directed to the use of perfluoroalkyl group-containing (meth-)acrylate esters in dental technology, particularly to the use of those compounds, which, as curable polymers, are suitable in dentistry for relining dental prostheses. More particularly, the invention is directed to curable dental preparations The term "(meth-)acrylate esters" is intended to indicate that methacrylate esters, as well as acrylate esters are embraced by the invention.

BACKGROUND INFORMATION AND PRIOR ART

Fluorine-containing monomeric and oligomeric (meth-)acrylates are known from the literature. They are used for the production of dental prostheses and filling materials and endow them with reduced water absorption and lower solubility For example, the use of 1,1,5-trihydro-octafluoropentyl methacrylate as a polymerizable component of dental filling compositions is described in the J. Dent. Res. 58, 1181 to 1186. Moreover, fluorine-containing phenylcarbinol acrylates, such as 1,1,1,3,3,3-hexafluoro-2-phenyl-2-acryloyloxy-propane, is known from the Org. Coat. Plast. Chem. 42, 204 to 207, 1980.

Furthermore, similar compounds and their use in the dental sector are disclosed in U.S. Pat. No. 4,356,296. The U.S. Pat. No. 4,616,072 discloses perfluoroalkyl monomethacrylates as hydrophobic copolymers for dental filling materials. The monomers with substituted bis-phenyltetrafluoroethane, which are disclosed in the EP-A2-0 201 031 and 0 201 778 are likewise used in restorative dentistry.

These previously known monomers have the disadvantage that, as they cure, essentially hard, brittle polymers result. This greatly limits the possibility of their being used in dental technology.

Perfluoroalkylalkoxyalkyl (meth-)acrylates and their polymers are also known. In the U.S. Pat. Nos. 3,600,360 and 4,080,507, these compounds are disclosed as water- and oil-repelling materials for various substrates. Uses in the dental sector are not known.

OBJECT OF THE INVENTION

It is an object of the invention to provide preparations of curable monomers for use in dental technology, which have a lower solubility and produce cured end products with a higher mechanical strength and can be used particularly as relining material for dental prostheses with increased adhesion to already cured polymethyl methacrylate. Generally, it is an object of the invention to improve on curable dental preparations.

SUMMARY OF THE INVENTION

The inventive dental preparations comprise as active ingredient (meth-)acrylate esters of the general formula

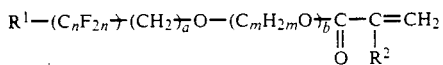
I wherein
- $R^1$ is the same or different and represents a hydrogen or fluorine group
- $R^2$ is the same or different and represents a hydrogen or methyl group,
- a has a value of 0, 1, 2, 3 or 4,
- b has an average value of 2 to 30
- n has an average value of 4 to 12 and
- m has an average value of 3 to 14.

Such compounds can be synthesized by known methods, such as those disclosed in the U.S. Pat. Nos. 3,660,360 and 4,080,507.

The above formula I is understood to be an average, general formula of a polymer mixture. The individual components differ particularly in the number of their oxyalkylene groups, which corresponds with the average value b as maximum to a Schulz-Flory distribution or approximates such a distribution. The chain length of the fluoroalkyl group is determined by the subscript n, which has an average value of 4 to 12. If the alcohol

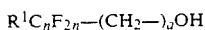

is a single compound, the value of n is absolute and corresponds to a whole number from 4 to 12. Preferred for the inventive use are compounds with an average or absolute value of n=6 to 10.

The hydroxyl function of the fluorinated alcohol may be separated from the perfluoroalkyl group by one or more $CH_2$ groups. The number of such $CH_2$ groups is determined by the value of a, which may be a whole number, namely 0, 1, 2, 3, or 4.

The subscript m of the oxyalkylene group $C_mH_{2m}O$— has an average value of 3 to 14. The oxyalkylene group may have the structure

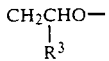

wherein $R^3$ is an alkyl group with 1 to 2 carbon atoms, or the structure $CH_2CH_2CH_2CH_2O$, if tetrahydrofuran is used for the synthesis of the fluorinated alkanol polyether.

Examples of suitable oxyalkylene groups are the oxypropylene, oxybutylene, oxyoctylene, oxydecylene and oxydodecylene group. The compounds for the inventive use may have the same or different oxyalkylene groups within the individual molecule, so that the subscript m is understood to be in the one case an absolute numerical value and, in the other, an average numerical value. If different oxyalkylene groups are present next to one another in the same molecule, whether arranged randomly (statistically) or in blocks, the molecule shall be free of oxyethylene groups. If the molecule has only the same oxyalkylene groups, that is, if the value of m is understood to be absolute, it follows from the lower limit of m=3 that oxyethylene groups are excluded.

Compounds, which contain the perfluoroalkyl groups, are, as a rule, insoluble or not very soluble in conventional solvents and are for that reason difficult to handle. Due to the presence of oxyalkylene groups with longer chain $R^3$ groups, the properties of the compounds, especially after the polymerization, such as the hydrophobicity and the elastic/plastic behavior as well as the solubility, can be influenced and adapted to the inventive application.

The number of oxyalkylene groups arises out of the value of b and, on the average, is 2 to 30 and preferably 5 to 20.

Particularly preferred for the inventive use are those compounds, in which in the average molecule at least 50 mole percent of the oxyalkylene units are oxypropylene and/or oxybutylene units and the average value of m in the remaining oxyalkylene units it 5 to 14. It has been ascertained that these compounds are particularly suitable for the inventive use.

Particularly preferred for the inventive use are compounds, in the average molecule of which, at least 90 mole percent of the oxyalkylene units are oxypropylene and/or oxybutylene units and in which the average value of m in the remaining oxyalkylene units is 5 to 14.

Compounds, in which the oxyalkylene units consist exclusively of oxypropylene and/or oxybutylene units, combine outstanding properties with low costs.

In the inventive use of the compounds as curable monomers in the dental sector, these are compounded with additives usually employed in dental technology. Such additives may be fillers, such as—particularly hydrophobized—glass-ceramics, finely divided silica or pigments or modifying agents. The function of the modifying agents is to optimize certain properties, which are important for the application, such as the elasticity, tear strength, ageing resistance and compatibility.

Further suitable modifying agents are divinylbenzene, ethylene glycol dimethacrylate, butanediol dimethacrylate, trimethylolpropane trimethacrylate and pentaerythritol tetramethacrylate.

Catalysts for the radiation-induced polymerization, such as benzil dimethyl ketal, 2,3-bornane dione, dimethylaminobenzenesulfanic acid bis(allyl amide), benzophenone and diethoxyacetophenone are furthermore added to the preparations in amounts of 0.1 to 3% by weight. The preparation is cured with the help of lights, which are normally used in dental technology and the radiation of which has a wave length of 200 to 550 nm.

The curing can also be carried out with peroxide catalysts or initiators at elevated temperatures. For this purpose, peroxides such as dibenzoyl peroxide are used. At low temperatures, cross linking with the help of redox initiators is possible. An example of such a redox initiator is the system of dibenzoyl peroxide/N,N-dihydroxyethyl-p-toluidine.

The compounding with various additives and the curing of the (meth)acrylate esters to dental products appropriate for the inventive use and optimized for the particular application are accomplished in known fashion, the details of which may be taken from the publications cited above, particularly the EP-A2-0 201 031 and 0 201 778.

The invention is described by the following Examples, it being understood that the Examples are given by way of illustration and not by way of limitation.

EXAMPLES

I. Synthesis of an α-Hydroxy-ω-Perfluoroalkylalkanol Polyether (Not of the Invention)

Perfluorooctylethanol (170 g, approximately 0.37 moles) and 9.2 g of tin tetrachloride are heated in a pressure reactor under pure nitrogen to 60° C. Over a period of 3 hours, 163 g (approximately 2.8 moles) of propylene oxide are added. The contents of the reactor are reacted out during a further 0.5 hour at the same temperature. The reaction product is then cooled. The epoxide number of 0.01, determined on a sample of the product, indicates that the reaction has gone largely to completion. The product is neutralized with 25% by volume ammonia, the water is distilled off from it at 80° C. and 10 torr and, finally, it is filtered in the presence of a filter aid.

The hydroxyl number, determined by wet analysis, is 63. Assuming a functionality of 1, this hydroxyl number corresponding to a molecular weight of approximately 890.

II. Synthesis of an α-Methacryloyl-ω-Perfluoroalkanol Polyether

The α-hydroxy-ω-perfluoroalkanol polyether (575 g, approximately 0.5 moles) from Example I and 0.4 g of 2,6-di-tert.-butylcresol are dissolved in 1,300 mL of dried chloroform. To this solution, 60 g of triethylamine are added and the whole is heated to 40° C. Now 53 g (approximately 0.5 moles) of methacryl chloride are carefully added dropwise. Stirring is continued for 15 hours at 50° C. Subsequently, the solution is washed twice with 0.1n HCl, four times with 5% sodium bicarbonate solution and repeatedly with distilled water, until it is neutral. The organic phase is dried with calcium chloride and concentrated under vacuum. A slightly yellow, liquid substance (612 g), with a theoretical molecular weight of 1219, is obtained. NMR spectrophotometric analysis reveals a degree of transesterification of 99%.

III. Preparation of a Relining Material for Dental Prostheses That Remains Soft The α-methacryloyl-ω-perfluoroalkanol polyether (60 parts by weight) is mixed with 35 parts by weight of 2,2,3,3-tetrafluoropropyl methacrylate and 5 parts by weight of perfluorononyl-1,2-diacrylate. To the mixture, 1.5% by weight of dibenzoyl peroxide is added.

Hydrophobic silica (35 parts by weight) is added to this solution by intensive mixing under vacuum in a laboratory planetary mixer. A clear, transparent paste results, which can be used by the press method as well as by the injection method as a soft relining material for dental prostheses. Curing takes place within 1 to 3 hours in the water bath at 70° to 90° C.

Curing is also possible within a few minutes in conventional commercial microwave ovens with subsequent storage for one hour at room temperature.

TABLE

| Example | Water Absorption mg/cm$^2$ | Shore A Hardness 37° C. |
|---|---|---|
| Of the Invention | 0.4 ± 0.1 | 28-33 |
| Commercial Product on Silicon Basis | 1.70 ± 0.80 | 30-35 |
| Commercial Product Based on Plasticized Methacrylate | 6.90 ± 1.20 | 47-50 |

We claim:

1. In a method of relining dental prostheses, wherein a curable dental preparation is applied to the prosthesis to be relined and is cured, the improvement which comprises that the curable dental preparation contains an effective amount of a (meth-)acrylate ester of the general formula

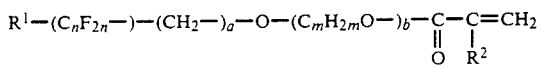
wherein
$R^1$ is the same or different and represents a hydrogen or fluorine group,
$R^2$ is the same or different and represents a hydrogen or methyl group,
a has a value of 0, 1, 2, 3 or 4,
b has an average value of 2 to 30,
n has an average value of 4 to 12, and
m has an average value of 3 to 14.
* * * * *

UNITED STATES PATENT AND TRADEMARK OFFICE
CERTIFICATE OF CORRECTION

PATENT NO. : 5,026,902

DATED : June 25, 1991

INVENTOR(S) : Jürgen Fock et al

It is certified that error appears in the above-identified patent and that said Letters Patent is hereby corrected as shown below:

Title page, item [54] and column 1, lines 2-4, should read

--DENTAL COMPOSITION OF PERFLUOROALKYL GROUP-CONTAINING (METH-)ACRYLATE ESTERS--.

Title page, item [73], should read --Th. Goldschmidt AG, Essen, Fed. Rep. of Germany & GDF Gesellschaft für Dentale Forschung u. Innovationen GmbH, Rosbach v.d.H., Fed. Rep. of Germany Signed and Sealed this Twentieth Day of April, 1993

Attest:

MICHAEL K. KIRK

*Attesting Officer*   Acting Commissioner of Patents and Trademarks